United States Patent [19]

Miyazaki

[11] Patent Number: 5,530,789
[45] Date of Patent: Jun. 25, 1996

[54] IMAGE PROCESSING APPARATUS AND METHOD FOR CONSTRUCTING A FUNCTIONAL IMAGE USING FEATURE AMOUNTS OF FUNCTIONS APPROXIMATING CHANGES IN IMAGE DATA ON A TIME AXIS

[75] Inventor: Osamu Miyazaki, Ibaraki-ken, Japan

[73] Assignee: Hitachi Medical Corporation, Tokyo, Japan

[21] Appl. No.: 141,537

[22] Filed: Oct. 27, 1993

[30] Foreign Application Priority Data

Oct. 29, 1992 [JP] Japan ................................. 4-291752

[51] Int. Cl.$^6$ .................................................. G06F 15/00
[52] U.S. Cl. .................... 395/101; 364/413.14; 378/901; 382/173; 128/661.08
[58] Field of Search .................................. 358/296, 135; 388/296; 382/56, 154, 166, 173; 250/363.04; 364/413, 14, 413.18; 378/4, 901, 21–23; 128/653.3, 661.01, 661.08, 661.09; 395/101, 106, 114

[56] References Cited

U.S. PATENT DOCUMENTS 4,809,350  2/1989  Shimoni et al. .......................... 382/56
4,862,359  8/1989  Trivedi et al. ...................... 364/413.05

Primary Examiner—Nancy Le
Assistant Examiner—Craig A. Hallacher
Attorney, Agent, or Firm—Antonelli, Terry, Stout & Kraus

[57] ABSTRACT

An image processing apparatus includes a device for reducing a matrix size of each of plural tomographic original images of one section of an object to be examined, the images being picked up with change of time, a device for performing a moving average process with respect to the data changed with time of each of the pixels of the obtained reduced image, the device for approximating the data changed with time of each pixel after the moving average process is done with a function, and a device for extracting a feature amount of the approximated function and creating a functional image on the feature amount.

16 Claims, 7 Drawing Sheets

IMAGE PROCESSING APPARATUS AND METHOD FOR CONSTRUCTING A FUNCTIONAL IMAGE USING FEATURE AMOUNTS OF FUNCTIONS APPROXIMATING CHANGES IN IMAGE DATA ON A TIME AXIS

BACKGROUND OF THE INVENTION

The present invention relates an image processing apparatus and method for constructing a functional image which image, is used for analyzing the motion of a fluid in tissue from plural images of one section of the tissue as measured by a medical apparatus, like an X-ray CT apparatus.

To dynamically analyze information about fluid moving in an object to be examined, it is necessary to continually pick up plural images of one part of the object for measuring a change in the part with the passage of time. For example, an X-ray CT apparatus continues to measure a target section of the object for several tens of seconds after a contrast medium is injected into the object. By reconstructing the measuring data as images, plural tomographic images of one and the same section of an object part can be obtained. Assuming that an apparatus designed to continuously do with-turn and one-second scans operates to measure a part of the object for thirty seconds, thirty time-serial CT images can be obtained.

As a method for analyzing the motion of a fluid in an object part to be examined based on such serial CT images, there has been proposed a method for obtaining an approximation of each pixel with a function and constructing an image of a feature amount of the approximate function. Concretely, the method takes the steps of obtaining an approximation with a gamma function and deriving a maximum value and the time needed to reach the maximum value for forming an image of the target diagnosis part. This image captures a functional feature of an object part to be examined (for example, blood flow). This image is thus referred to as a functional image.

In this method, image noise and operating time are inhibitive factors. The image noise is likely to inhibit the ability to execute a proper approximation, thereby lowering the quality of a functional image. More and higher definitive images result in expanding each image matrix and increasing the amount of data, thereby increasing the operating time.

Another problem is an exposure against an object to be examined, though it actually depends on the necessary amount of data. The improved performance of an X-ray CT apparatus makes it possible to measure a target object part plural times at short intervals for the purpose of capturing the motion of fluid. However, it is necessary to emit sufficient radioactive rays for achieving a sufficient image quality at each measuring time. Hence, the amount of radioactive rays is increased with an increase of the measuring time.

SUMMARY OF THE INVENTION

It is an object of the present invention to provide an image processing apparatus and method for constructing a functional image for analyzing the motion of a fluid in an object to be examined which apparatus and method enable an improvement in the quality of the functional image, reduce the operating time and produce an excellent image even if the interval of measurement between adjacent images is long.

In carrying out this object, the apparatus according to the present invention includes a device for reducing a matrix size of each of plural tomographic original images of one and the same section of the object to be examined, those images being picked up with change of time, a device for taking a moving average of data on the change of time at each pixel of the reduced image, and a device for defining an approximate section standing for a data group used for functional approximation of the data changed with time of each pixel after the moving average of the data is done, estimating data outside of the approximate section, and approximating the estimated data and the data at the approximate interval with a function, and a device for extracting a feature amount of the approximated function and constructing a functional image.

Moreover, the apparatus according to the invention provides a device for interpolating the image data between measurement of an image and that of an adjacent image even if the interval therebetween is long.

In addition, the apparatus according to the invention provides a device for expanding the matrix size when observing the resulting functional image.

According to the present invention, the reduction of an image results in decreasing the number of pixels to be approximated with a function, thereby shortening the operating time. Further, the moving averaging process serves to remove noise components for enhancing the image quality.

According to the present invention, if the images to be taken are small in number, the interpolation offers the necessary data for doing the functional approximation. If, therefore, the intervals between measurements of the adjacent images are relatively long, the resulting functional image maintains a quality which is sufficiently high.

In addition, the necessary image data captured by the interpolation makes it possible to reduce the amount of radioactive rays to be radiated to the object.

DESCRIPTION OF THE PREFERRED EMBODIMENTS

Figure 1:
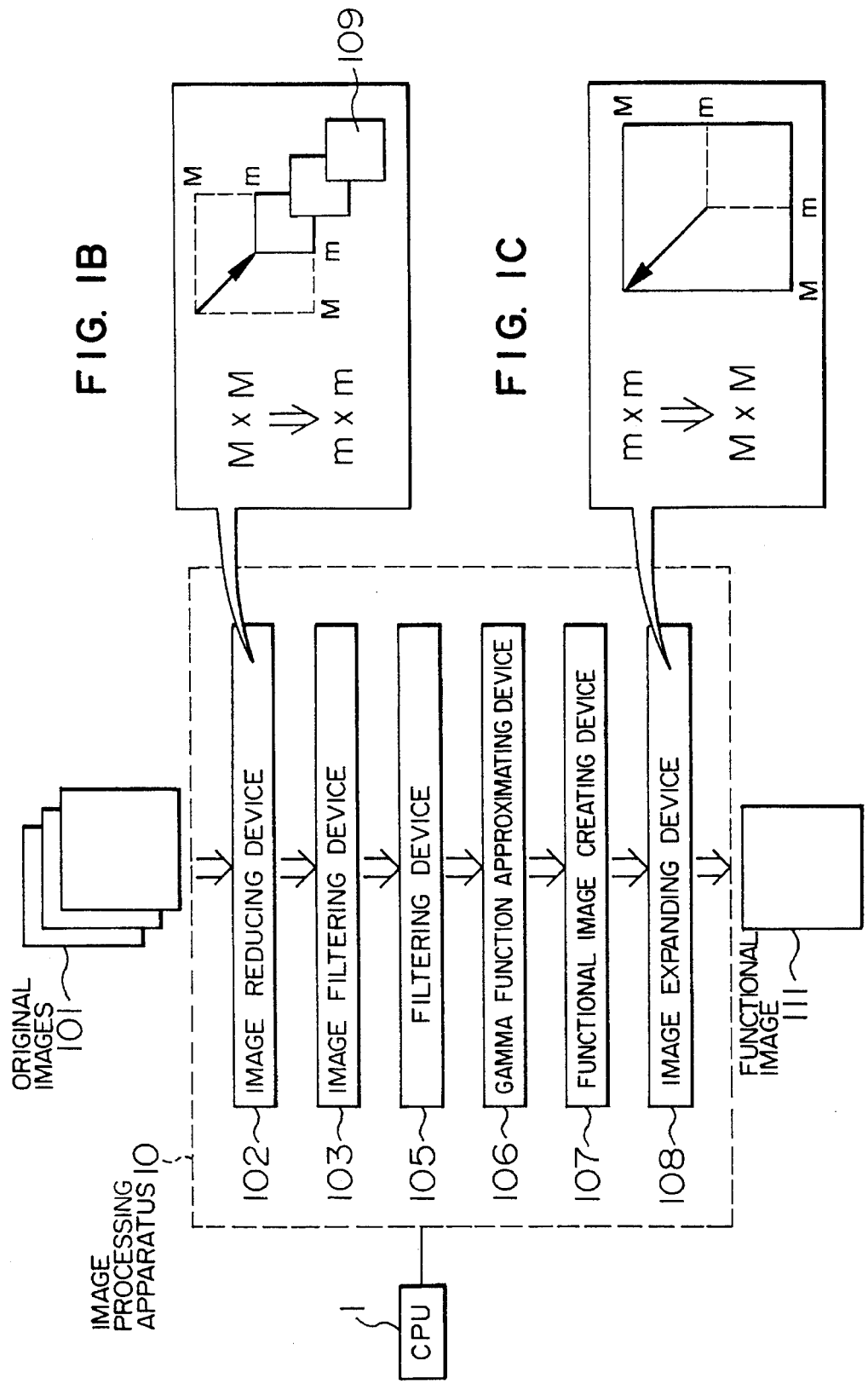
FIG. 1A is a diagram showing an image processing apparatus according to an embodiment of the present invention.
FIG. 1B is a view showing how a matrix size is reduced.
FIG. 1C is a view showing how a matrix size is expanded.

This embodiment is directed to an example in which blood flow is analyzed from a contrast CT image (original image) obtained by an X-ray CT apparatus.

An image processing apparatus according to this embodiment is shown in FIG. 1A. A numeral 101 designates group of original images which are serially taken for thirty seconds at the rate of each scan for one second. Hence, the original image 101 is a group of thirty images serially arranged along an axis of time. The image processing apparatus 10 is arranged to have an image reducing device 102 for reducing an original image 101, an image filtering device 103 for filtering image data of an image, a filtering device 105 for filtering data captured with change of time, a gamma function approximating device 106 for approximating an image with a gamma function, a functional image creating device 107, and an image expanding device 108 for expanding the data of a functional image. Each device is controlled by a CPU 1 or a CPU built in each device.

The image reducing device 102 serves to reduce each of the thirty original images 101 as shown in FIG. 1B. For example, it is assumed that one image is composed of pixels consisting of 1024×1024. The pixel matrix is reduced to 512×512 (a quarter). For the reduction, the averaging method is used. For example, two adjacent pieces of data may be simply averaged and the averaged value derived as image data at the location. Three or more adjacent pieces of data may be averaged. Further, a square image area having the same number of pixels on each side may be averaged. In addition, a thinning method may be used for the reduction. The thinning, however, impairs the reliability of the image data itself (increases the image noise). Such operations thus have to be improved. The reduced image is denoted by 109 (see FIG. 1B).

The image filtering device 103 is used for controlling noise within each reduced image. For example, the device 103 uses a two-dimensional Gaussian filter. With this filtering, a reduced image to be properly analyzed can be constructed.

The filtering device 105 performs a moving average process (a kind of filtering) with respect to the image data formed with time, obtained at a corresponding pixel unit in each reduced image 109. This moving average process serves to suppress noises appearing due to motion of a patient with the passage of time. Herein, the term "moving average process" means a processing method of taking an average value of a (for example, three) pieces of data containing a center pixel and the other pixels located before and after the center pixel itself as moving the device one pixel by one pixel along an axis of time and setting the average value as the image data of the central pixel. In this case, therefore, the image data of each pixel is replaced with the average value of three pieces of image data containing the pixel and the pixels before and after the pixel itself.

In general, to grasp the feature of motion of fluid moving in tissue, the measured data concerning the fluid is approximated with a gamma function.

The gamma function approximating device 106 is composed of a data estimating unit and a function approximating unit. The data estimating unit defines a data range (section) to be approximated with a function and extrapolates the data outside of the section from the data inside of the section for deriving the data outside of the section. The function approximating unit finds the most suitable gamma function with which the estimated data and the image data changing with time, concretely, the data inside of the section, may be approximated. The method of approximation adopts the method of least squares and is executed to find a gamma function in which an error of square in the method of least squares is suppressed to a minimum.

The gamma function f(t) is;

$$f(t)=k(t-t_0)^\alpha \exp\{-(t-t_0)/\beta\} \tag{1}$$

This gamma function f(t) is fixed by four parameters, that is, coefficients k, $t_0$, $\alpha$, $\beta$. Finding the approximate gamma function means finding a gamma function (expression 1) changing most closely with respect to the image data at that time. It also means finding the concrete values of the four parameters k, $t_0$, $\alpha$, $\beta$. The selection of the gamma function results from an objective that it is preferable to obtain a functional image of blood flow.

Hence, the four parameters are defined at each pixel (i, j) of the reduced image as follows.

Pixel (1, 1) . . . $k_{11}$, $t_{011}$, $\alpha_{11}$, $\beta_{11}$
Pixel (1, 2) . . . $k_{12}$, $t_{012}$, $\alpha_{12}$, $\beta_{12}$,
Pixel (i, j) . . . $k_{ij}$, $t_{0ij}$, $\alpha_{ij}$, $\beta_{ij}$, where i and j are defined in the range of $1 \leq i \leq 512$ and $1 \leq j \leq 512$.

The functional image creating device 107 operates to extract a feature amount of the gamma function from the four parameters k, $t_0$, $\alpha$, $\beta$ obtained at each of all the pixels and create a functional image. For example, to derive a time when the gamma function becomes maximum as a parameter on which a change of the regional blood flow is reflected, the time when the gamma function becomes maximum (peak time) is defined by the following expression with the three parameters $t_0$, $\alpha$, $\beta$.

$$PT(i, j)=-(\alpha_{ij}/\beta_{ij})+t_{0ij} \tag{2}$$

With this equation, the PTs for all the pixels are obtained by deriving three parameters $t_0$, $\alpha$, $\beta$ for all the pixels.

The pixel expanding device 108 operates to expand the functional image into the original image as shown in FIG. 1C. This operation makes it possible to obtain a functional image 111 expanded to the size of the original image so that the pixel may be displayed in visually sufficient size. This expansion is carried out by interpolation of the pixels.

Figure 2:
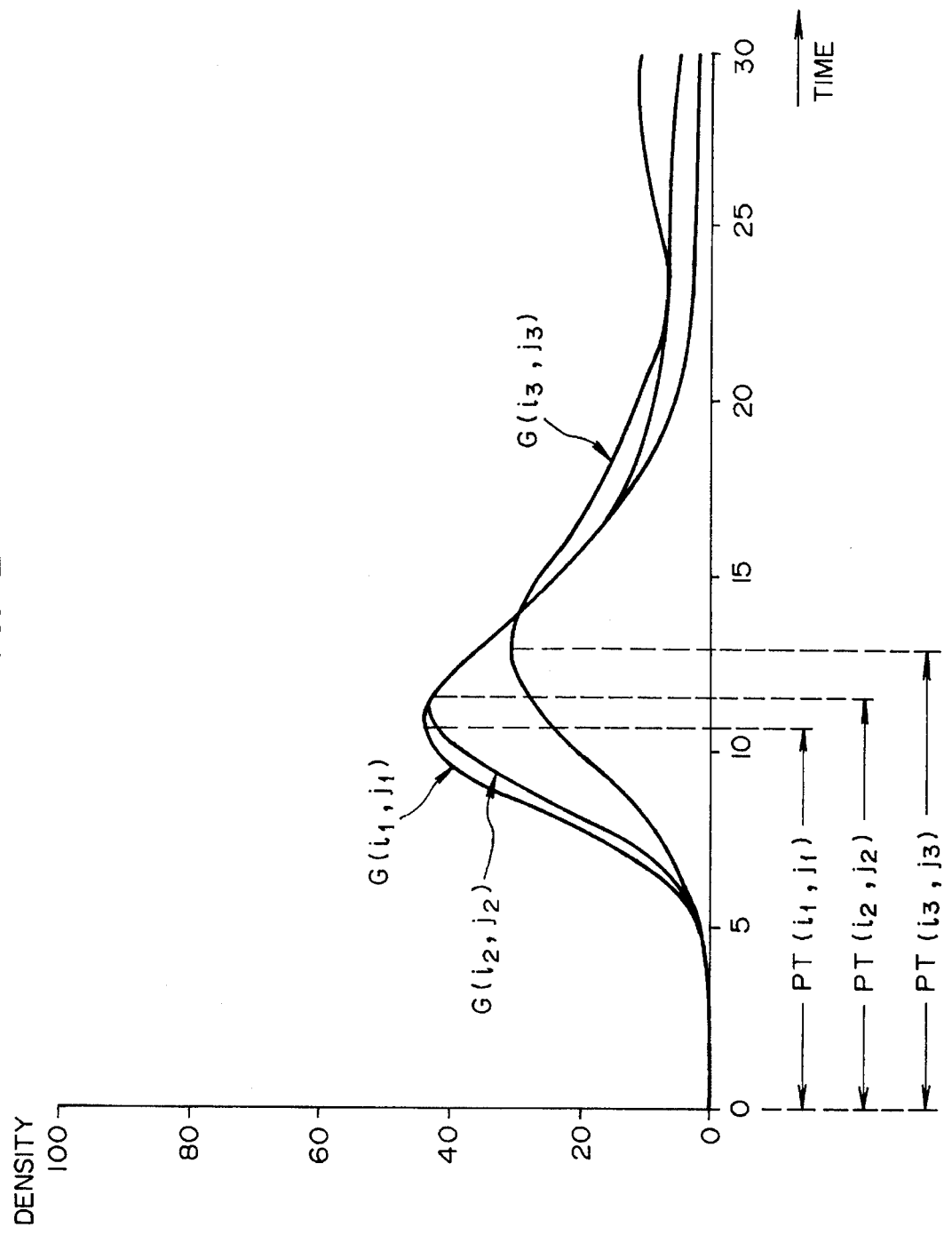
FIG. 2 is a graph showing approximation of pixels with a gamma function.

The gamma function provided by the functional image creating device 107 is shown in FIG. 2, in which the abscissa shows time and the ordinate shows size (density) of image data. In FIG. 2, $G(i_1, j_1)$, $G(i_2, j_2)$ and $G(i_3, j_3)$ denote the approximate gamma functions at the pixels $(i_1, j_1)$, $(i_2, j_2)$ and $(i_3, j_3)$, respectively. That is, for each pixel, the approximate gamma function characterized by the four parameters (k, $t_0$, $\alpha$, $\beta$) can be derived. In the expression 2, the peak times PT $(i_1, j_1)$, PT$(i_2, j_2)$ and PT $(i_3, j_3)$ of the approximate gamma functions are as shown in FIG. 2.

The PTs obtained for all the pixels form one functional image. In addition, there exist various other kinds of feature amounts for obtaining a functional image, such as the area and the maximum value of the gamma function.

In measuring blood flow, the image data measured with change of time contains a re-circulated blood flow. The data to be approximated is a blood flow containing no re-circulated blood flow in the measured data. Concretely, it is a data group for constructing the first peak. This data group is defined as a primary blood flow. In the approximation of the gamma function, it is necessary to avoid reflection of an adverse effect of the re-circulation of blood flow. For that purpose, it is possible to estimate the time when the re-circulation is started and use the data immediately before the estimated time for the approximation.

Figure 3:
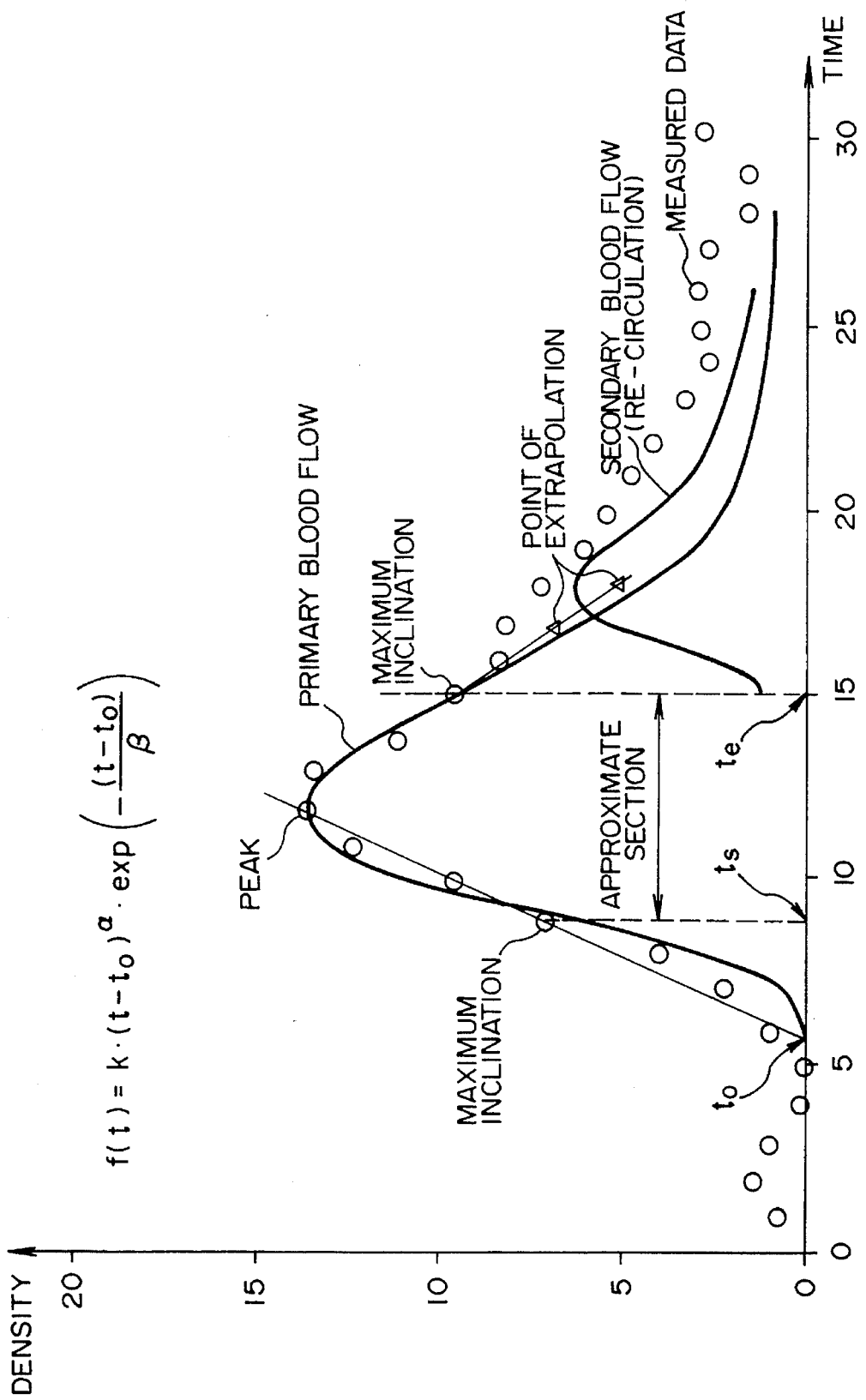
FIG. 3 is a graph showing a concrete gamma function used for approximation according to the present invention.

Around the rising part, it is difficult to distinguish the noise from the data. To correctly distinguish the noise, it is preferable that the proper number of sections are set for the approximation. An example concerning one pixel is shown in FIG. 3. Herein, each circle denotes measured data in a respective one of the thirty reduced images for the given pixel. The approximate section between $t_s$ and $t_e$ is set on the primary blood flow. In the set section, a gamma function is approximated. Outside of the approximate section, no gamma function is approximated. It is understood from FIG. 3 that no gamma function is described on the measured data, while the gamma function is properly described on the measured data inside the approximate section.

In the part outside of the approximate section, the data estimating unit provided in the gamma function approximating device serves to replace $t_0$ in the expression (1) (a rising time of the gamma function) or data in the case of no re-circulation of blood flow for doing proper approximation even in the outside part.

To describe the data estimating unit in more detail with reference to FIG. 3, the data estimating unit derives a point where an inclination of data changing with time becomes maximum and, for example, sets an approximate section between the maximum inclination points each containing the maximum value.

Further, a point $t_0$ is defined as a point of intersection between the time axis and a line connecting a peak point with the maximum inclination point on the increasing density side. In place, the data in case of no re-circulation may be estimated by using the data near the wash-out maximum inclination point. The maximum inclination point may be used for estimation. Or, a point around the maximum inclination point may be used as the point $t_0$. As mentioned above, by estimating the data from a far larger maximum value than the noise level or the maximum inclination point, a correct estimation is made possible.

Figure 4:
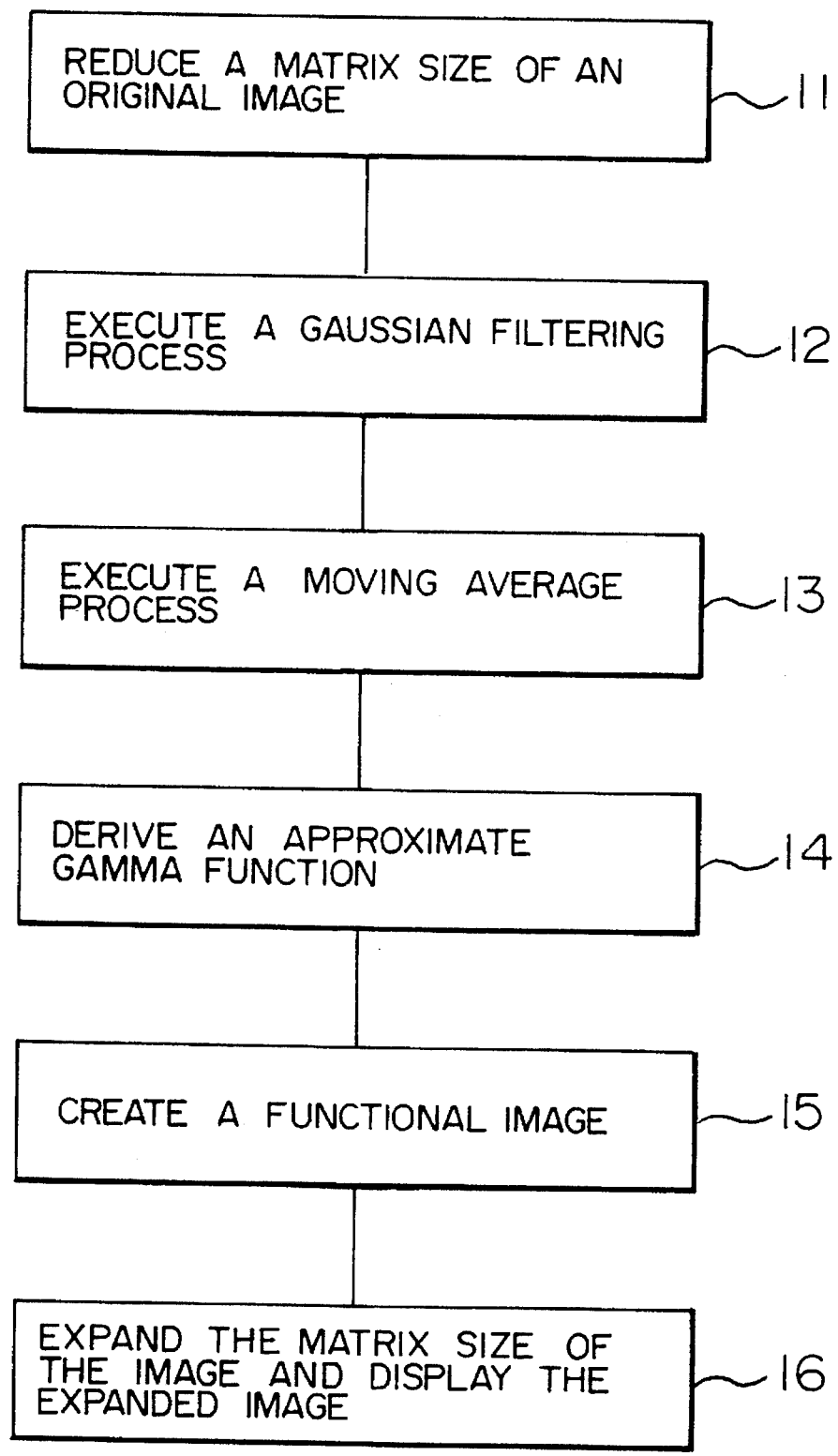
FIG. 4 is a flowchart showing an image processing routine according to the embodiment shown in FIG. 1.

FIG. 4 is a flowchart showing the procedure shown in FIG. 1.

At a step 11, a matrix (M×M) of an original image is reduced to a smaller matrix (m×m) (see FIG. 1B). At a step 12, the Gaussian filtering at the matrix of n×n is executed with respect to the reduced image, where n<m. At a step 13, the moving average process is executed with respect to the image data. The image data picked up with change of time is obtained for each pixel. This moving average process serves to remove noises resulting from motion of the object to be examined. At a step 14, an operation is executed to search for the most suitable gamma function G for approximating the resulting image data. At a step 15, the feature amount of the approximate function is extracted for creating a functional image of a matrix size (m×m). At a step 16, the functional image of a matrix size (m×m) is expanded to the matrix size (M×M) and is displayed on the screen so that an observer may more easily view it (see FIG. 1C).

Figure 5:
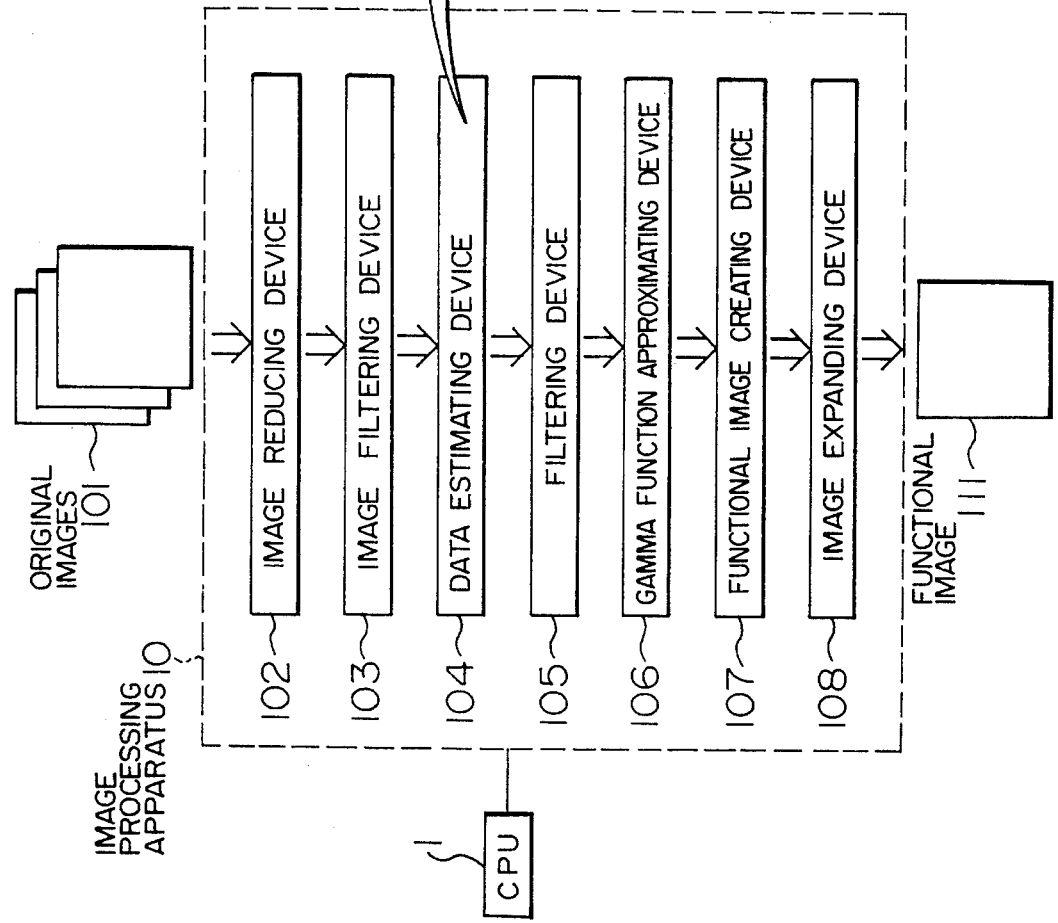
FIG. 5A is a diagram showing an image processing apparatus according to another embodiment of the present invention.
FIG. 5B is a view showing how an interpolation is executed in the embodiment shown in FIG. 5A.

FIG. 5A is a diagram showing an image processing apparatus according to another embodiment of the present invention. The image processing apparatus according to this embodiment is suitable for the case in which the interval of measurement between adjacent images is relatively long. If the interval of measurement between adjacent images is long, the number of pieces of measured data along an axis of time is small. To overcome this shortcoming, the apparatus of this embodiment makes up for the shortage of data through the effect of an image interpolating method. As shown in FIG. 5B, the filled images derived by the interpolating method are shown as interpolated data 110 by oblique lines.

Figure 6:
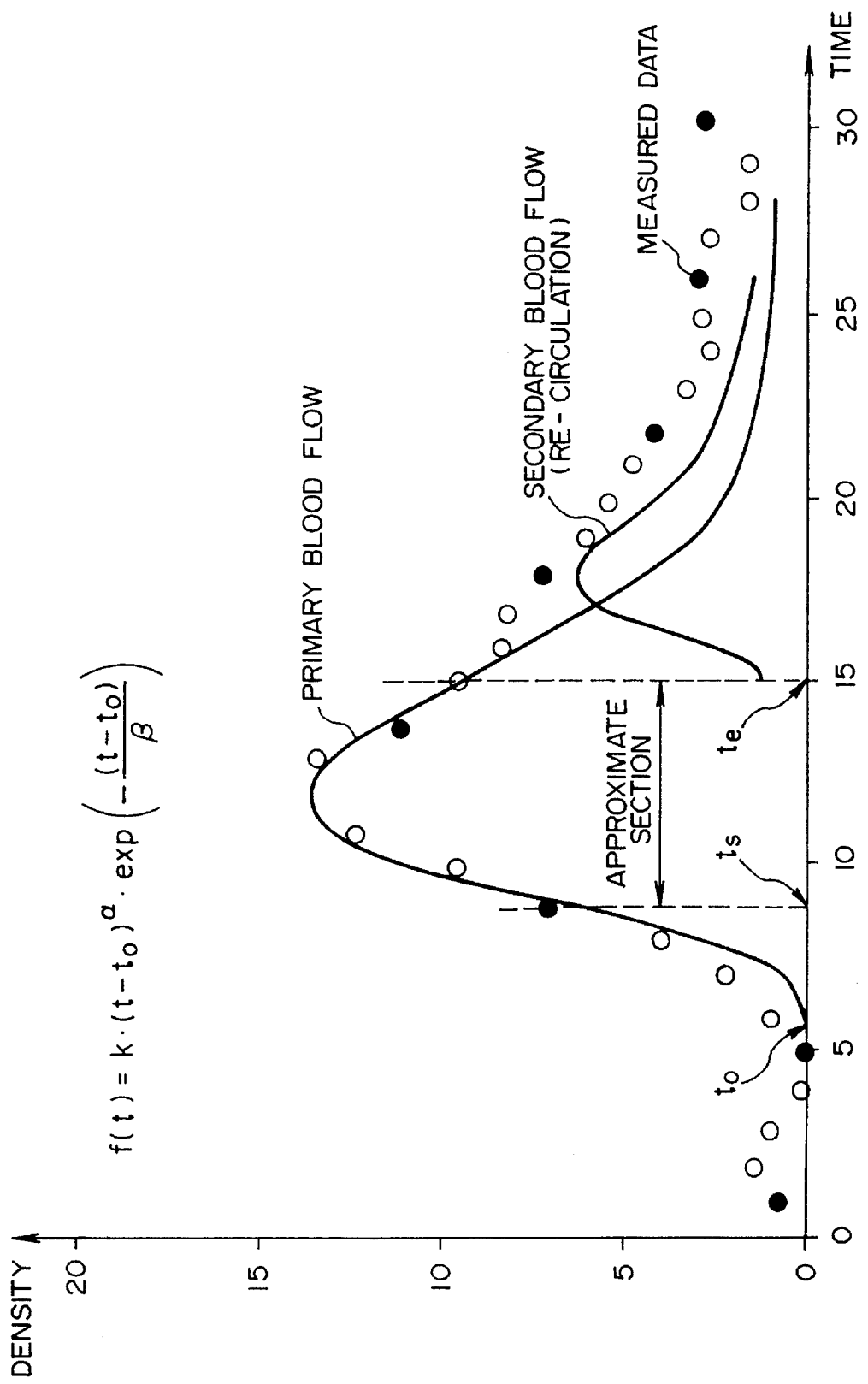
FIG. 6 is an explanatory graph showing the interpolation shown in FIG. 5B.

FIG. 6 is a flowchart for explaining the interpolating process executed by the image processing apparatus shown in FIG. 5A. In the embodiment shown in FIG. 6, eight measurements of one-second scan are executed at four-second intervals. This embodiment thus offers eight measured images. In FIG. 6, a black dot denotes actual measured data. A white dot denotes interpolated data. This interpolation, as shown, fills three dots between the adjacent measured data. Then, an approximate section ts-te is set against the image data picked up with change of time, the image data configured of the measured data and the interpolated data. On the section ts-te, a functional image is derived like the embodiment shown in FIG. 1.

Figure 7:
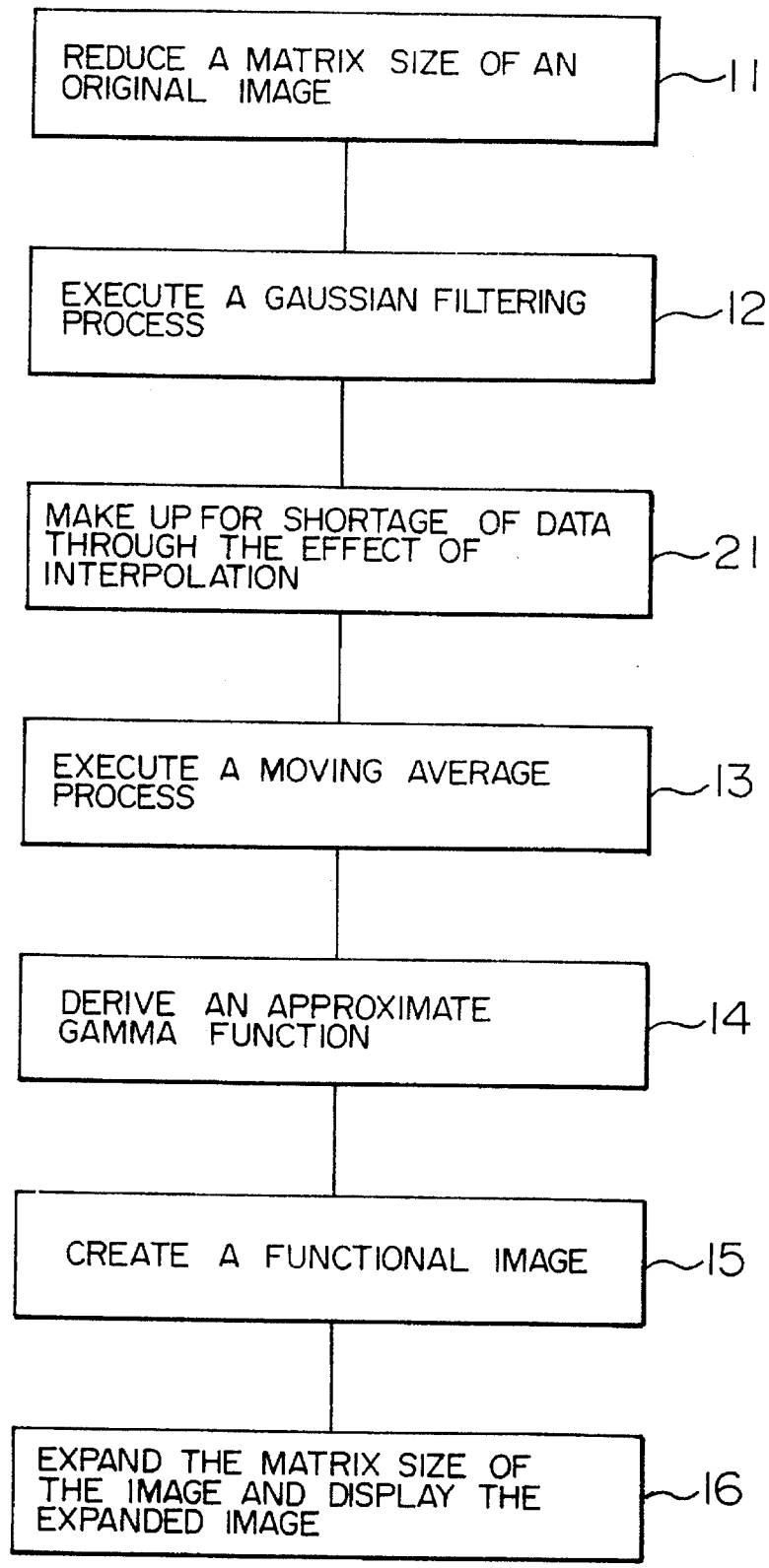
FIG. 7 is a flowchart showing an image processing routine executed in the embodiment shown in FIG. 5A.

FIG. 7 is a flowchart showing a flow of image processing. As shown, a step 21 for estimating shortage of data through the effect of the interpolation is newly added between the step 12 for doing the Gaussian filtering and the step 13 for doing the moving average process in the flow shown in FIG. 4. The other part of the flow is the same as the process shown in FIG. 4.

According to the present invention, in place of the gamma function, another function may be used for the approximation. For example, a Kety & Schmidt function used in the CBF analysis method (regional cerebral blood flow analysis method) may be used as well. In addition, variable reduction factors of a reduced image or variable expanding factors of an expanded image may be employed.

What is claimed is:

1. An image processing apparatus for processing a group of tomographic images obtained at different times by repeatedly scanning a section of an object to be examined, said tomographic images each being formed by a matrix of pixels, said apparatus comprising:

means for reducing the size of each of the tomographic images of said group to produce reduced images;

means for performing a moving average process on image data of corresponding pixels in each of the reduced images;

means for determining a section of the data of each of the pixels processed by said moving average process along a time axis;

means for estimating data outside of said section for each pixel processed by said moving average process by extrapolation on said time axis;

means for determining a function approximating changes in said estimated data and in said data in said section;

means for extracting a feature amount of said function approximating said changes; and means for forming a functional image based upon said extracted feature amount.

2. An image processing apparatus according to claim 1, wherein said reducing means comprises means for reducing the number of pixels in each of said tomographic images by a predetermined amount to reduce the matrix size thereof.

3. An image processing apparatus according to claim 1, wherein said extracting means extracts as a feature amount one of peak time, area and maximum value of said function.

4. An image processing apparatus according to claim 1, wherein said estimating means includes a data estimating unit for defining said section of the data and for estimating data outside said section, and said function determining means includes a function approximating unit for determining a gamma function which approximates said estimated data outside said section and said data inside said section.

5. An image processing apparatus according to claim 1, further comprising means for expanding the size of said functional image.

6. An image processing apparatus according to claim 1, further comprising means for deriving said image data by interpolation between pixels in each of said reduced images.

7. An image processing method for processing a group of tomographic images obtained at different times by repeatedly scanning a section of an object to be examined, said tomographic images each being formed by a matrix of pixels, said method comprising the steps of:

reducing the size of each of the tomographic images of said group to produce reduced images;

performing a moving average process on image data of corresponding pixels in each of the reduced images;

determining a section of the data of each of the pixels processed by said moving average process along a time axis;

estimating data outside of said section for each pixel processed by said moving average process by extrapolation on said time axis;

determining a function approximating changes in said estimated data and in said data in said section;

extracting a feature amount of said function approximating said changes; and forming a functional image based upon said extracted feature amount.

8. An image processing method according to claim 7, wherein the size of said tomographic images is reduced by reducing the number of pixels therein by a predetermined amount to reduce the matrix size thereof.

9. An image processing method according to claim 7, wherein said extracting step extracts as a feature amount one of peak time, area and maximum value of said function.

10. An image processing method according to claim 7, wherein said estimating step includes defining said section of the data and estimating data outside said section, and said function determining includes determining a gamma function which approximates said estimated data outside said section and said data inside said section.

11. An image processing method according to claim 7, further comprising the step of expanding the matrix size of said functional image.

12. An image processing method for processing a group of tomographic images obtained at different times by repeatedly scanning a section of an object to be examined, said tomographic images each being formed by a matrix of pixels, said method comprising the steps of:

reducing the size of each of the tomographic images of said group to produce reduced images;

deriving image data by interpolation between pixels in each of said reduced images;

performing a moving average process on said image data of corresponding pixels in each of the reduced images;

determining a section of the data of each of the pixels processed by said moving average process along a time axis;

estimating data outside of said section for each pixel processed by said moving average process by extrapolation on said time axis;

determining a function approximating changes in said estimated data and in said data in said section;

extracting a feature amount of said function approximating said changes; and forming a functional image on based upon said extracted feature amount.

13. An image processing method according to claim 12, wherein the size of said tomographic images is reduced by reducing the number of pixels therein by a predetermined amount to reduce the matrix size thereof.

14. An image processing method according to claim 12, wherein said extracting step extracts as a feature amount one of peak time, area and maximum value of said function.

15. An image processing method according to claim 12, wherein said estimating step includes defining said section of the data and estimating data outside said section, and said function determining includes determining a gamma function which approximates said estimated data outside said section and said data inside said section.

16. An image processing method according to claim 12, further comprising the step of expanding the matrix size of said functional image.

\* \* \* \* \*